United States Patent
Ma et al.

(10) Patent No.: US 9,863,895 B1
(45) Date of Patent: Jan. 9, 2018

(54) SYSTEMS AND METHODS FOR MONITORING CASING CEMENT INTEGRITY

(71) Applicants: Saudi Arabian Oil Company, Dhahran (SA); Weatherford International, LLC, Houston, TX (US)

(72) Inventors: Shouxiang Mark Ma, Dhahran (SA); Darryl Trcka, Fort Worth, TX (US); Robert Wilson, Mancos, CO (US)

(73) Assignees: Saudi Arabian Oil Company, Dhahran (SA); Weatherford International, LLC, Houston, TX (US)

( * ) Notice: Subject to any disclaimer, the term of this patent is extended or adjusted under 35 U.S.C. 154(b) by 0 days.

(21) Appl. No.: 15/438,956

(22) Filed: Feb. 22, 2017

(51) Int. Cl.
| G01V 3/00 | (2006.01) |
| G01N 23/02 | (2006.01) |
| G01V 5/10 | (2006.01) |
| E21B 47/00 | (2012.01) |

(52) U.S. Cl.
CPC ........... *G01N 23/025* (2013.01); *E21B 47/00* (2013.01); *G01V 5/108* (2013.01)

(58) Field of Classification Search
CPC ....... G01N 23/025; E21B 47/00; G01V 5/108
USPC .......... 340/856.3; 367/7, 35; 166/253.1, 249
See application file for complete search history.

(56) References Cited

U.S. PATENT DOCUMENTS

| 2,515,501 A | 7/1950 | Fearon et al. |
| 2,515,534 A | 7/1950 | Thayer et al. |
| 2,543,675 A | 2/1951 | Swift |
| 2,953,685 A | 9/1960 | Dewan |
| 2,963,582 A | 12/1960 | Lebourg |
| 3,019,341 A | 1/1962 | Monaghan |
| 3,521,063 A | 7/1970 | Tittman |
| 4,057,720 A * | 11/1977 | Paap .................... E21B 47/1015 250/266 |

(Continued)

FOREIGN PATENT DOCUMENTS

| GB | 948310 | 1/1964 |
| RU | 2447265 C1 | 4/2012 |
| WO | 2013012504 A2 | 1/2013 |

OTHER PUBLICATIONS

Adolph et al.; "Saturation Monitoring With the RST Reservoir Saturation Tool" Oilfield Review, Jan. 1994, pp. 29-39.

(Continued)

*Primary Examiner* — Ojiako Nwugo
(74) *Attorney, Agent, or Firm* — Bracewell LLP; Constance G. Rhebergen; Christopher L. Drymalla

(57) ABSTRACT

Provided in some embodiments are systems and methods for monitoring cement quality of a cased well. Embodiments include conducting a cement-bond logging and a first pulsed neutron (PN) logging to generate a cement-bond log (CBL) and first pulsed neutron log (PNL) for the well, determining a first cement quality index (CQI) for the well based on the CBL and the first PNL, in response to determining that mud effects for the well have dissipated, conducting a second PN logging to generate a second PNL for the well, determining a second CQI for the well based on the CBL and the second PNL, determining a tuned CQI for the well based on the first CQI and the second CQI, conducting a follow-up PN logging to generate a follow-up PNL for the well, and determining a cement quality log for the well based on the tuned CQI and the follow-up PNL.

21 Claims, 6 Drawing Sheets

(56) References Cited

U.S. PATENT DOCUMENTS

| | | | |
|---|---|---|---|
| 4,071,757 A * | 1/1978 | Arnold | E21B 47/1015 |
| | | | 250/265 |
| 4,587,424 A | 5/1986 | Grau | |
| 5,045,692 A | 9/1991 | Arnold | |
| 5,094,808 A | 8/1992 | Meeh | |
| 5,237,594 A | 8/1993 | Carroll | |
| 5,377,753 A * | 1/1995 | Haberman | E21B 28/00 |
| | | | 166/177.6 |
| 5,406,078 A | 4/1995 | Jacobson | |
| 5,656,930 A | 8/1997 | Hagiwara | |
| 5,900,733 A | 5/1999 | Wu et al. | |
| 6,936,812 B2 | 8/2005 | Odom et al. | |
| 7,059,404 B2 | 6/2006 | Flecker et al. | |
| 7,925,443 B2 | 4/2011 | Wahrmund et al. | |
| 8,800,653 B2 | 8/2014 | Dria | |
| 8,964,504 B2 | 2/2015 | Chace | |
| 8,975,574 B2 | 3/2015 | Hulszoon Cornelis | |
| 2006/0102834 A1 | 5/2006 | Mickael | |
| 2007/0011115 A1 * | 1/2007 | Smith, Jr. | G06N 3/0454 |
| | | | 706/15 |
| 2007/0150201 A1 | 6/2007 | Eidesmo et al. | |
| 2010/0126718 A1 * | 5/2010 | Lilley | E21B 37/00 |
| | | | 166/253.1 |
| 2011/0238313 A1 | 9/2011 | Thornton | |
| 2013/0105678 A1 | 5/2013 | Wilson | |
| 2013/0119245 A1 | 11/2013 | Difoggio | |
| 2013/0299687 A1 | 11/2013 | Scott et al. | |
| 2014/0052376 A1 * | 2/2014 | Guo | E21B 47/00 |
| | | | 702/11 |
| 2015/0090871 A1 | 4/2015 | Chace | |
| 2015/0137987 A1 * | 5/2015 | Donderici | G01V 1/48 |
| | | | 340/856.4 |
| 2015/0168581 A1 * | 6/2015 | Izuhara | E21B 47/0005 |
| | | | 702/9 |
| 2015/0369956 A1 * | 12/2015 | Ma | E21B 47/12 |
| | | | 250/269.7 |
| 2016/0018548 A1 * | 1/2016 | McCafferty | G01V 1/40 |
| | | | 367/7 |
| 2016/0047238 A1 | 2/2016 | Zeroug et al. | |
| 2016/0061021 A1 * | 3/2016 | Shaposhnikov | E21B 47/0005 |
| | | | 367/35 |
| 2016/0320523 A1 * | 11/2016 | Inanc | G01V 5/145 |

OTHER PUBLICATIONS

Albertin et al.; "The Many Facets of Pulsed Neutron Cased-Hole Logging" Oilfield Review, Summer 1996, pp. 28-41.

Badruzzaman et al.; "Multi-Sensor Through-Casing Density and Saturation Measurement Concepts With a Pulsed Neutron Source: A Modeling Assessment" SPE 89884, SPE International Petroleum Conference, Nov. 7-9, 2004, Puebla Pue., Mexico, pp. 1-14.

Co-Pending U.S. Appl. No. 14/310,540 (SA5275), filed Jun. 20, 2014, pp. 1-53.

Eyvazzadeh et al.; "An Innovative Application to Reduce Petrophysical Uncertainty in Reservoir Monitoring: Case Studies from Gian Saudi Arabian Fields" SPE 97519, SPE International Improved Oil Recovery Conference, Dec. 5-6, 2005, Malaysia, pp. 1-8.

Gilchrist, Jr., et al.; "Introduction of a New Through-Tubing Multifunction Pulsed Neutron Instrument" SPE 56803, Society of Petroleum Engineers, SPE Annual Conference & Exhibition, Oct. 3-6, Houston, TX, pp. 1-11.

International Search Report and Written Opinion for PCT/US2015/035123 (SA5275/PCT) dated Jan. 28, 2016.

Jacobson et al.; "A New Small-Diameter, High-Performance Reservoir Monitoring Tool" SPWLA paper K, Society of Petrophysicists and Well-Log Analysts, SPWLA 39th Annual Logging Symposium, May 26-29, 1998, Keystone, CO, pp. 1-14.

Jacobson et al.; "Carbon/Oxygen Tool Response in Open Hole" SPWLA paper RR, Society of Petrophysicists and Well-Log Analysts, SPWLA 46th Annual Logging Symposium, Jun. 26-29, 2005, New Orleans, LA, pp. 1-11.

Khan et al.; "Advances in Pulse Neutron Capture in Evaluating Formation Properties within Low Permeability Carbonates Reservoir Onshore Abu Dhabi: An Integrated Case Study" SPE-182985-MS, Abu Dhabi, UAE, Nov. 7-10, 2016, pp. 1-13.

Wu et al.; "Monte Carlo Simulating of Three Detector Density Logging" Chinese Journal of Geophysics, vol. 47, No. 1, 2004, pp. 181-187.

Zett et al.; "Surveillance of Complex Displacement Mechanisms in Mature Reservoirs to Maximize Recovery" SPE 159185, Society of Petroleum Engineers, SPE Annual Technical Conference & Exhibition, Oct. 8-12, 2012, San Antonio, TX, pp. 1-9.

* cited by examiner

SYSTEMS AND METHODS FOR MONITORING CASING CEMENT INTEGRITY

FIELD OF INVENTION

The present invention relates generally to determining characteristics of wells, and more particularly to assessing and monitoring integrity of cement in cased wellbores.

BACKGROUND OF THE INVENTION

A petroleum reservoir is a subsurface pool of hydrocarbons (e.g., oil or gas) trapped in a subsurface rock formation. Oil and gas wells are often drilled into petroleum reservoirs to extract (or "produce") the trapped hydrocarbons. It can be beneficial to understand the characteristics of a well when making critical decisions regarding completion and production of the well. For example, characteristics of the reservoir, such as reservoir saturation, can be used to determine whether the formation contains hydrocarbons, to estimate an amount of hydrocarbons or water in the formation, to predict the ability to produce the hydrocarbons, to determine optimal techniques for drilling and producing the hydrocarbons via the well, and so forth. Moreover, characteristics of the components of the well, such as the structural integrity of the well's casing, casing cement, and the like can be used to determine how the well is performing and what, if any, operations are needed to improve the performance of the well.

Well characteristics can be determined using a variety of different techniques. For example, certain well characteristics can be determined via coring or logging operations. Coring operations include the physical extraction of rock samples for assessment at the surface. Logging operations are performed to assess the formation and other components of the well down-hole. Logging operations typically include lowering one or more logging tools into a wellbore of a well, and recording measurements as the tool traverses the wellbore. This can be accomplished via wireline logging, logging-while-drilling (LWD), measurement-while-drilling (MWD), and/or the like. A plot of the measurements versus depth is typically referred to as a "log". Logs can be analyzed to determine characteristics of the well and the reservoir, such as reservoir water saturation.

There are many types of logging available, and a particular form of logging may be selected and used based on the logging conditions and the type of measurements to be acquired. For example, pulsed neutron (PN) logging operations measure absorption of neutrons by the wellbore and the reservoir area around a wellbore. This absorption measurement can be used to determine characteristics of the well and the reservoir, such as water saturation ($S_w$) of the reservoir. PN logging tools often employ a source to emit bursts of high energy neutrons that are absorbed by nuclei in the wellbore and the formation around the wellbore, and detectors to measure gamma rays output by the nuclei as a result of absorbing the neutrons. The gamma ray population is observed to decay for each burst to determine absorption of the neutrons, and the determined absorption can be used to generate corresponding water saturation values and a water saturation log for the well. As another example, acoustic based cement-bond (CB) logging measures acoustic amplitude attenuation. This amplitude attenuation measurement can be used to determine characteristics of the well, such as a degree of coupling of cement to the casing and the formation. CB logging tools often employ one or more acoustic transmitters to emit an acoustic wave that propagates into the casing, the cement and the formation, and two or more acoustic receivers to measure resulting acoustic waves. Characteristics of the resulting acoustic waves, such as amplitude, can be used to determine the structural integrity of the cement, including its bond to the casing and the formation.

SUMMARY OF THE INVENTION

Applicants have recognized that, although assessment of cement quality is typically done shortly after casing a well, current techniques do not provide for simple and cost-effective monitoring cement quality deterioration over time. For example, a first assessment of cement quality may be accomplished by running an acoustic based cement-bond (CB) logging tool into a cased wellbore after cementing the casing, but before production tubing or other completion components are inserted into the casing, to generate a first CB log. Once the completion components are inserted in the casing, however, follow-up CB logging operations may require pulling out the completion components (e.g., using a workover rig which is costly and time-consuming) and re-running a CB logging tool through the wellbore to generate another CB log. Once the CB logging operation is completed, the completion components may, again, be lowered into the wellbore to resume production or similar operations. Accordingly, follow-up CB logging procedures can be both time consuming and costly. As a result, well operators may have to incur the delay and cost associated with conducting CB monitoring operations, or most often elect to forgo follow-up cement quality assessment.

Applicants have recognized that the limitations of CB monitoring may be due to the large size of acoustic logging tools that does not allow the tools to be run into a wellbore with tubing and other completion equipment in place. Applicants have also recognized that, although some current logging and log analysis techniques can be useful for determining some well characteristics (e.g., including characteristics of the reservoir penetrated by the well), certain well characteristics can be skewed by environmental factors, such as the quality of a well's casing cement. For example, although reservoir water saturation ($S_w$) for a well can be estimated using certain logging and log analysis techniques, such as PN logging, the determinations can be skewed by the properties of the cement located in a casing-borehole annulus (CBA) between the casing and the formation. Moreover, the cement can deteriorate over time, further contributing to skewed estimates of the well characteristics over time.

Recognizing these and other shortcomings of existing systems, Applicants have developed novel systems and methods for monitoring well characteristics, including cement quality and/or reservoir water saturation, over time. In some embodiments, cement quality monitoring includes determining a cement quality for a well based on multiple pulsed neutron (PN) logging operations conducted over an extended period of time, and saturation monitoring includes determining water saturation for the well based on results of the cement quality monitoring. For example, cement quality monitoring may include the following: (1) drilling a well; (2) casing the well (e.g., setting casing in a borehole of the well that extends across a target reservoir and cementing the casing in place by disposing cement in a CBA located between the outer diameter (OD) of the casing and the surface of the formation forming the wall of the borehole of the well); (3) conducting an initial CB logging operation shortly after casing the well (e.g., less than 1 week after casing the well) to generate an initial cement quality log (CQL) for the well; (4) conducting a first/initial pulsed neutron (PN) logging operation shortly after casing the well (e.g., less than 1 week after casing the well and/or within a few days of the CB logging operation) to generate a first/initial PN log (PNL) for the well; (5) calibrating the first PNL with the initial CQL to derive a first baseline cement quality index (CQI) (e.g., defining relationships between normalized carbon-oxygen ratios (C/O)n and cement quality ($\Phi$); and (6) in response to determining that mud effects for the well have been reduced or eliminated (e.g., in response to determining that a given amount of time has passed and/or the well is perforated and/or production or injection operations have commenced), conducting a second PN logging operation to generate a second PNL for the well; (7) generating a tuned CQI based on the baseline CQI and the second PNL; and (8) periodically conducting follow-up cement monitoring operations that each include the following: (a) conducting a follow-up PN logging operation to generate a follow-up PNL for the well; (b) determining an updated cement quality log (CQL) for the well based on the follow-up PNL for the well. Further, saturation monitoring may include determining an updated $S_w$ log for the well based on the follow-up PNL and/or the updated CQL for the well. A $S_w$ log can be used, for example, to determine the concentration of water and/or hydrocarbons at the various depth intervals along the length of the well. This information can be used to make various determinations regarding operating and characterizing the well. For example, where the $S_w$ log indicates a relatively high water saturation along a cased interval of the wellbore of a well, a follow-up completion operation can be conducted to seal-off nearby portions of the wellbore to prevent water breakthrough at that location, thereby inhibiting the water for mixing with produced hydrocarbons. Also, a production estimate for the well can be adjusted lower to account for the realization that water is moving closer to the producing intervals of the well. As a result, enhanced recovery operations, such as injection operations can be conducting in an effort to inhibit the movement of the water in the formation toward to the producing intervals of the well.

Provided in some embodiments is a method for monitoring cement quality of a cased well. The method includes: conducting a cement-bond (CB) logging of a well to generate cement-bond log (CBL) for the well, the well including: a wellbore penetrating a subsurface formation; casing disposed in the wellbore; and cement disposed in a casing-borehole annulus (CBA) located between the casing and the formation; conducting a first pulsed neutron (PN) logging of the well to generate a first pulsed neutron log (PNL) for the well, the first PNL indicating carbon-oxygen ratios $((C/O)_1)$ for the well at the time of the first PN logging; determining a first baseline cement quality index (CQI) for the well based on the CBL and the first PNL, the first baseline CQI including a first mapping of cement qualities to normalized carbon-oxygen ratios $((C/O)_{N1})$ (e.g., with potential near wellbore reservoir saturation alteration caused by drilling mud filtrate invasion); determining that mud effects for the well present at the time of the first PN logging of the well have dissipated; in response to determining that mud effects have dissipated, conducting a second PN logging of the well to generate a second PNL for the well, the second PNL indicating carbon-oxygen ratios $((C/O)_2)$ for the well at the time of the second PN logging (e.g., when near wellbore reservoir saturation has been restored back to close to its original value which is the representative to reservoir saturation); determining a second baseline CQI for the well based on the CBL and the second PNL, the second baseline CQI including a second mapping of cement qualities to normalized carbon-oxygen ratios $(C/O)_N$, (e.g., when near wellbore reservoir saturation is representative to the target reservoir); determining a tuned CQI for the well based on the first baseline CQI and the second baseline CQI, the tuned CQI including a third mapping of cement qualities to normalized carbon-oxygen ratios; conducting a follow-up PN logging of the well to generate a follow-up PNL for the well, the follow-up PNL indicating carbon-oxygen ratios for the well at the time of the follow-up PN logging; and determining an updated cement quality log (CQL) for the well based on the tuned CQI and the follow-up PNL, the updated CQL including a mapping of cement quality values versus depth in the wellbore.

In certain embodiments, the method includes determining an updated water saturation log for the well based on follow-up PNL. In some embodiments, determining an updated water saturation ($S_w$) log for the well based on follow-up PNL includes determining an initial $S_w$ log for the well based on the follow-up PNL, and adjusting water saturation values of the initial $S_w$ log based on corresponding cement quality values of the updated CQL to generate the updated $S_w$ log. In certain embodiments, the follow-up PN logging of the well is conducted without removing completion components from the wellbore of the well. In some embodiments, determining that mud effects for the well present at the time of the first PN logging of the well have dissipated includes determining that at least a threshold amount of time has passed since casing the well. In certain embodiments, determining that mud effects for the well present at the time of the first PN logging of the well have dissipated includes determining that at least one year has passed since casing the well. In some embodiments, determining that mud effects for the well present at the time of the first PN logging of the well have dissipated includes determining that a perforation, a production or an injection operation for the well has been ongoing for at least a threshold amount of time. In certain embodiments, the first, second, and follow-up PN loggings of the well are conducted using a multi-detector (MD) PN logging tool. In some embodiments, the MD PN tool includes a single PN source and multiple (e.g., five) PN detectors. In certain embodiments, the method includes determining that a portion of the cement at a location is deteriorated based on the updated CQL; and conducting a remediation operation to improve the quality of the cement in the location.

Provided in some embodiments is a method for monitoring cement quality of a cased well. The method includes: obtaining, by well controller system, a cement-bond log (CBL) for a well, the CBL obtained via a cement-bond logging of the well conducted after casing the well and when mud effects for the well are present, the well including: a wellbore penetrating a subsurface formation; casing disposed in the wellbore; and cement disposed in a casing-borehole annulus (CBA) located between the casing and the formation; obtaining, by the well control system, a first pulsed neutron log (PNL) for the well, the first PNL obtained via a first pulsed neutron (PN) logging of the well conducted after casing the well and at a time when mud effects for the well are present; determining, by the well control system, a first baseline cement quality index (CQI) for the well based on the CBL and the first PNL, the first baseline CQI including a first mapping of cement qualities to normalized carbon-oxygen ratios; obtaining, by the well control system, a second PNL for the well, the second PNL obtained via a second PN logging of the well conducted after casing the well, after the first PN logging of the well, and at a time when the mud effects for the well are not present; determining, by the well control system, a second baseline CQI for the well based on the CBL and the second PNL, the second baseline CQI including a second mapping of cement qualities to normalized carbon-oxygen ratios; determining, by the well control system, a tuned CQI for the well based on the first baseline CQI and the second baseline CQI, the tuned CQI including a third mapping of cement qualities to normalized carbon-oxygen ratios; obtaining, by the well control system, a follow-up PNL for the well, the follow-up PNL obtained via a follow-up PN logging of the well conducted after the second PN logging of the well, the follow-up PNL indicating carbon-oxygen ratios for the well at the time of the follow-up PN logging of the well; and determining, by the well control system, an updated cement quality log (CQL) for the well based on the tuned CQI and the follow-up PNL for the well, the updated CQL including a mapping of cement quality values versus depth in the wellbore.

In certain embodiments, the method includes determining an updated water saturation ($S_w$) log for the well based on follow-up PNL. In some embodiments, determining an updated $S_w$ log for the well based on follow-up PNL includes determining an initial $S_w$ log for the well based on the follow-up PNL, and adjusting water saturation values of the initial $S_w$ log based on corresponding cement quality values of the updated CQL to generate the updated $S_w$ log. In certain embodiments, the follow-up PN logging of the well is conducted without removing completion components from the wellbore of the well. In some embodiments, the second PN logging of the well is conducted at least a threshold amount of time after casing the well. In certain embodiments, the second PN logging of the well is conducted at least a one year after casing the well. In some embodiments, the second PN logging of the well is conducted after a perforation, a production or an injection operation for the well has been ongoing for at least a threshold amount of time. In certain embodiments, the first, second, and follow-up PN loggings of the well are conducted using a multi-detector (MD) PN logging tool. In some embodiments, the MD PN tool includes a single PN source and multiple (e.g., five) PN detectors.

Provided in some embodiments is a system for monitoring cement quality of a cased well. The system includes: a well control system adapted to: obtain a cement-bond log (CBL) for a well, the CBL obtained via a cement-bond (CB) logging of the well conducted after casing the well and when mud effects for the well are present, the well including: a wellbore penetrating a subsurface formation; casing disposed in the wellbore; and cement disposed in a casing-borehole annulus (CBA) located between the casing and the formation; obtain a first pulsed neutron log (PNL) for the well, the first PNL obtained via a first pulsed neutron (PN) logging of the well conducted after casing the well and at a time when mud effects for the well are present; determine a first baseline cement quality index (CQI) for the well based on the CBL and the first PNL, the first baseline CQI including a first mapping of cement qualities to normalized carbon-oxygen ratios; obtain a second PNL for the well, the second PNL obtained via a second PN logging of the well conducted after casing the well, after the first PN logging of the well, and at a time when the mud effects for the well are not be present; determine a second baseline CQI for the well based on the CBL and the second PNL, the second baseline CQI including a second mapping of cement qualities to normalized carbon-oxygen ratios; determine a tuned CQI for the well based on the first baseline CQI and the second baseline CQI, the tuned CQI including a third mapping of cement qualities to normalized carbon-oxygen ratios; obtain a follow-up PNL for the well, the follow-up PNL obtained via a follow-up PN logging of the well conducted after the second PN logging of the well, the follow-up PNL indicating carbon-oxygen ratios for the well at the time of the follow-up PN logging of the well; and determine an updated cement quality log (CQL) for the well based on the tuned CQI and the follow-up PNL for the well, the updated CQL including a mapping of cement quality values versus depth in the wellbore.

In some embodiments, the system further includes one or more multi-detector (MD) pulsed neutron (PN) logging tools adapted to be run in a wellbore of a well to acquire log data for use in generating one or more PN logs (PNLs), and the first PN logging of the well is conducted using at least one of the one or more MD PN logging tools, the second PN logging of the well is conducted using at least one of the one or more MD PN logging tools, and the follow-up PN logging of the well is conducted using at least one of the one or more MD PN logging tools.

Figure 1:
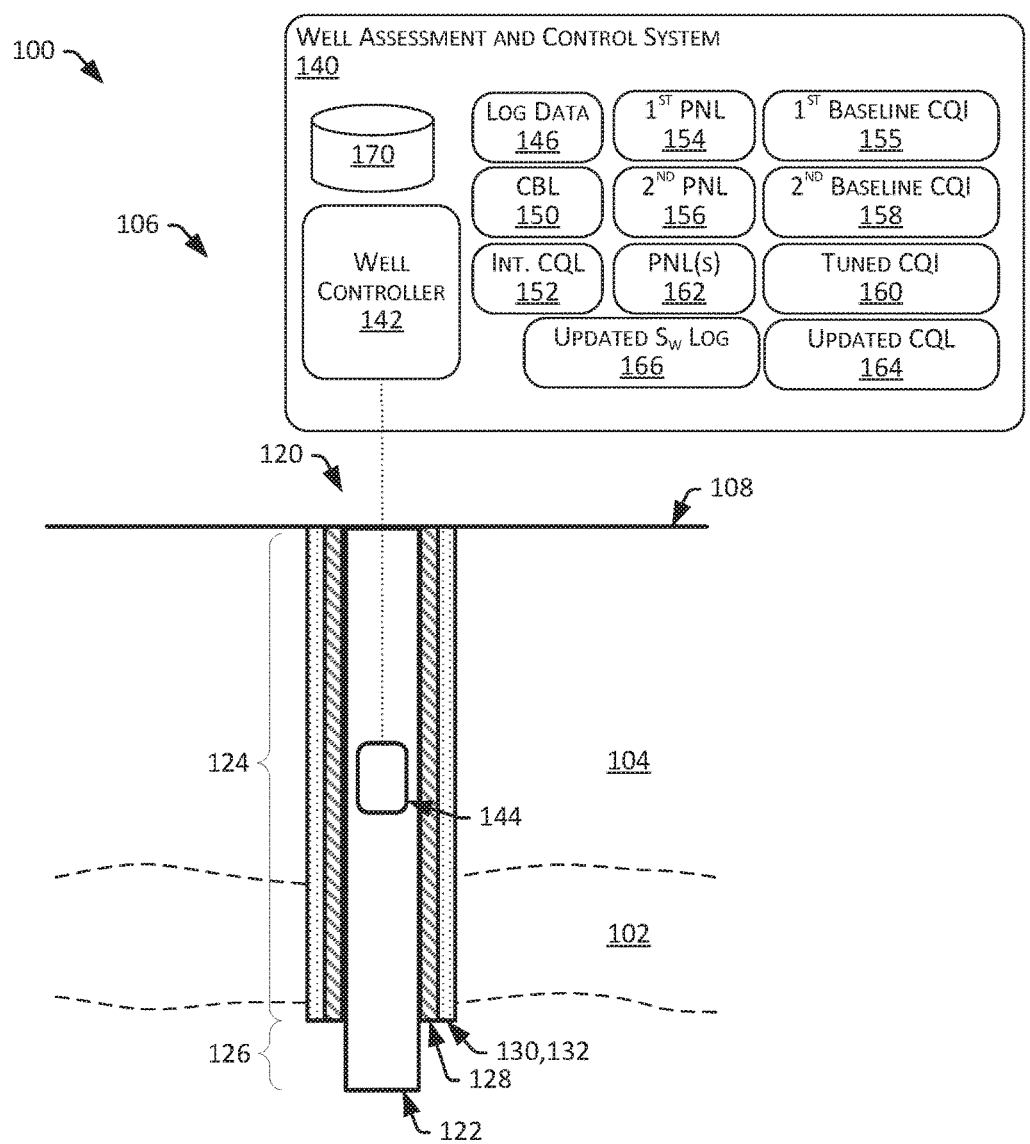
FIG. 1 is diagram that illustrates a well environment (including a well assessment and control (WAC) system) in accordance with one or more embodiments.

While this disclosure is susceptible to various modifications and alternative forms, specific embodiments thereof are shown by way of example in the drawings and will be described in detail herein. The drawings may not be to scale. It should be understood, however, that the drawings and the detailed descriptions thereto are not intended to limit the disclosure to the particular form disclosed, but, to the contrary, the intention is to cover all modifications, equivalents, and alternatives falling within the spirit and scope of the present disclosure as defined by the appended claims.

DETAILED DESCRIPTION

The present invention will now be described more fully hereinafter with reference to the accompanying drawings in which example embodiments of the invention are shown. This invention may, however, be embodied in many different forms and should not be construed as limited to the illustrated embodiments set forth herein, rather, these example embodiments are provided so that this disclosure will be thorough and complete, and will fully convey the scope of the invention to those skilled in the art.

Described herein are embodiments of systems and methods for monitoring well characteristics, including cement quality and/or reservoir water saturation, over time. In some embodiments, cement quality monitoring includes determining a cement quality for a well based on multiple pulsed neutron (PN) logging operations conducted over an extended period of time, and saturation monitoring includes determining water saturation for the well based on results of the cement quality monitoring. For example, cement quality monitoring may include the following: (1) drilling a well; (2) casing the well (e.g., setting casing in a borehole of the well that extends across a target reservoir and cementing the casing in place by disposing cement in a casing-borehole annulus (CBA) located between the outer diameter (OD) of the casing and the surface of the formation forming the wall of the borehole of the well); (3) conducting an initial CB logging operation shortly after casing the well (e.g., less than 1 week after casing the well) to generate an initial cement quality log (CQL) for the well; (4) conducting a first/initial pulsed neutron (PN) logging operation shortly after casing the well (e.g., less than 1 week after casing the well and/or within a few days of the CB logging operation) to generate a first/initial PN log (PNL) for the well; (5) calibrating the first PNL with the initial CQL to derive a first baseline cement quality index (CQI) (e.g., defining relationships between normalized carbon-oxygen ratios (C/O) and cement quality ($\Phi$); and (6) in response to determining that mud effects for the well have been reduced or eliminated (e.g., in response to determining that a given amount of time has passed and/or the well is perforated and/or production or injection operations have commenced), conducting a second PN logging operation to generate a second PNL for the well; (7) generating a tuned CQI based on the baseline CQI and the second PNL; and (8) periodically conducting follow-up cement monitoring operations that each include the following: (a) conducting a follow-up PN logging operation to generate a follow-up PNL for the well; (b) determining an updated cement quality log (CQL) for the well based on the follow-up PNL for the well. Further, saturation monitoring may include determining an updated $S_w$ log for the well based on the follow-up PNL and/or the updated CQL for the well.

FIG. 1 is a diagram that illustrates a well environment 100 in accordance with one or more embodiments. In some embodiments, the well environment 100 includes a petroleum reservoir (a "reservoir") 102 located in a subsurface formation (a "formation") 104, and a production system 106 for producing hydrocarbons from the reservoir 102.

The formation 104 may include porous or fractured rock formations that reside underground, beneath the earth's surface 108. The reservoir 102 may include a portion of the formation 104 that contains (or at least determined or expected to contain) a subsurface pool of hydrocarbons, such oil and/or gas. The reservoir 102 may include different layers of rock have varying characteristics, including varying degrees of permeability, porosity, resistivity, and/or the like.

In some embodiments, the production system 106 includes a well to facilitate extraction of hydrocarbons from the reservoir 102. For example, in the illustrated embodiment, the production system 106 includes a well 120 having a wellbore 122 that extends into the formation 104 and the reservoir 102. In some embodiments, some or all of the portions of the wellbore 122 are cased (e.g., including an annular casing) or open-holed (e.g., not including an annular casing). For example, in the illustrated embodiment, the wellbore 122 includes a cased portion 124 and an open-hole portion 126. In some embodiments, the cased portion 124 includes casing 128 that extends downward from the surface 108. The casing 128 may include, for example, an annular casing, such as a hollow cylindrical metal pipe (e.g., a steel pipe) that extends into the wellbore 122. In some embodiments, the cased portion 124 includes one or more layers of cement 130 located in a casing-borehole annulus (CBA) 132. The CBA 132 may include a volume located between an outer diameter (OD) of the casing 128 and the surface of the formation 104 forming the wall of the wellbore 122. In a casing operation, a setting operation may be conducted to set the casing 128 in the wellbore 122, and a cementing operation may be conducted to dispose the cement 130 in the CBA 132. In a cementing operation, the cement 130 may be pumped down through a hollow interior of the casing 128 and around a bottom opening of the casing 128 such that the cement 130 is forced up the CBA 132 around the exterior of the casing 128 to seal the CBA 132 of the wellbore 122. Such a casing operation may provide structural integrity for the well 120 (e.g., ensuring that that the formation 104 does not collapse into the wellbore 122) and/or isolation of zones of the reservoir (e.g., ensuring that the flow path of the well 120 through the interior of the casing 128 is isolated from formation fluids in the adjacent portions of the formation 104, that high or low pressure zones in the adjacent portions of the formation 104 are isolated from one another, and so forth). In some embodiments, the casing 128 includes multiple intervals of casing successively placed within the previous casing run. For example, the casing 128 may include a production liner disposed inside of a production casing disposed inside of an intermediate casing disposed inside of a surface casing and/or conductor casing disposed inside of the surface casing.

In some embodiments, the production system 106 includes a well assessment and control (WAC) system, such as WAC system 140 illustrated in FIG. 1. The WAC system 140 may provide for monitoring the well 102 and controlling well operations to optimize drilling of the well and/or extraction of hydrocarbons from the reservoir 102 via the well 102. In some embodiments, the WAC system 140 includes a well controller 142 and one or more logging tools 144. The well controller 142 may provide for collection of log data 146 from the logging tool(s) 144 and/or processing of the log data 146 to determine various characteristics of the well 102, including the quality of the cement 130, water saturation ($S_w$) for the well 120, and/or the like. In some embodiments, log data 146 and/or the results of the processing may be stored in a memory, such as a database 170. This can include, for example, a CB log (CBL) 150, an initial cement quality log (initial CQL) 152, a first PNL 154, a first baseline CQI 155, a second PNL 156, a second baseline CQI 158, a tuned CQI 160, one or more follow-up PNLs 162, one or more updated CQLs 164, one or more updated water saturation logs ($S_w$ logs) 166, and/or the like. In some embodiments, the well controller 142 includes a computer system for performing some or all of the operations described herein, including those described with regard to the well controller 142. The well controller 142 may include a computer system that is the same or similar to the computer system 1000, described below.

In some embodiments, the one or more logging tools 144 include a CB logging tool for acquiring an acoustic cement-bond log for the well 120. For example, the one or more logging tools 144 may include CB logging tool configured to measure acoustic amplitude attenuation that can be used to determine a degree of coupling of the cement 130 to the casing 128 and/or the formation 104. The CB logging tool may include and employ one or more acoustic transmitters (e.g., ultrasonic transmitters) to emit an acoustic wave (e.g., an ultrasonic wave) that propagates into the casing 128, the cement 130 and/or the formation 104, and two or more acoustic receivers to measure resulting acoustic waves. Characteristics of the resulting acoustic waves, such as the wave amplitudes, can be used to determine the structural integrity of the cement 130, including its bond to the casing 128 and/or the formation 104, voids in the cement 130, and/or the like. In some embodiments, the CBL 150 is generated based on log data 146 corresponding to the measurements acquired by the CB logging tool during a CB logging operation.

In some embodiments, the one or more logging tools 144 include a PN logging tool for acquiring a PN log (PNL) for the well 120. For example, the one or more logging tools 144 may include a multi-detector (MD) PN logging tool configured to measure absorption of neutrons that can be used to determine water saturation and other characteristics for the well 120. The MD PN logging tool may include and employ a PN source to emit bursts of high energy neutrons that are absorbed by nuclei in the formation 104, and multiple PN detectors to measure gamma rays output by the nuclei as a result of absorbing the neutrons. The gamma ray population may be observed to decay for each burst to determine absorption of the neutrons. A corresponding PNL and/or $S_w$ log for the well 120 may be determined based on the absorption. As described herein, in some embodiments, the $S_w$ log for the well 120 may be corrected/adjusted based on a cement quality log (CQL) for the well 120 determined based on the PNL for the well 120.

Figure 2:
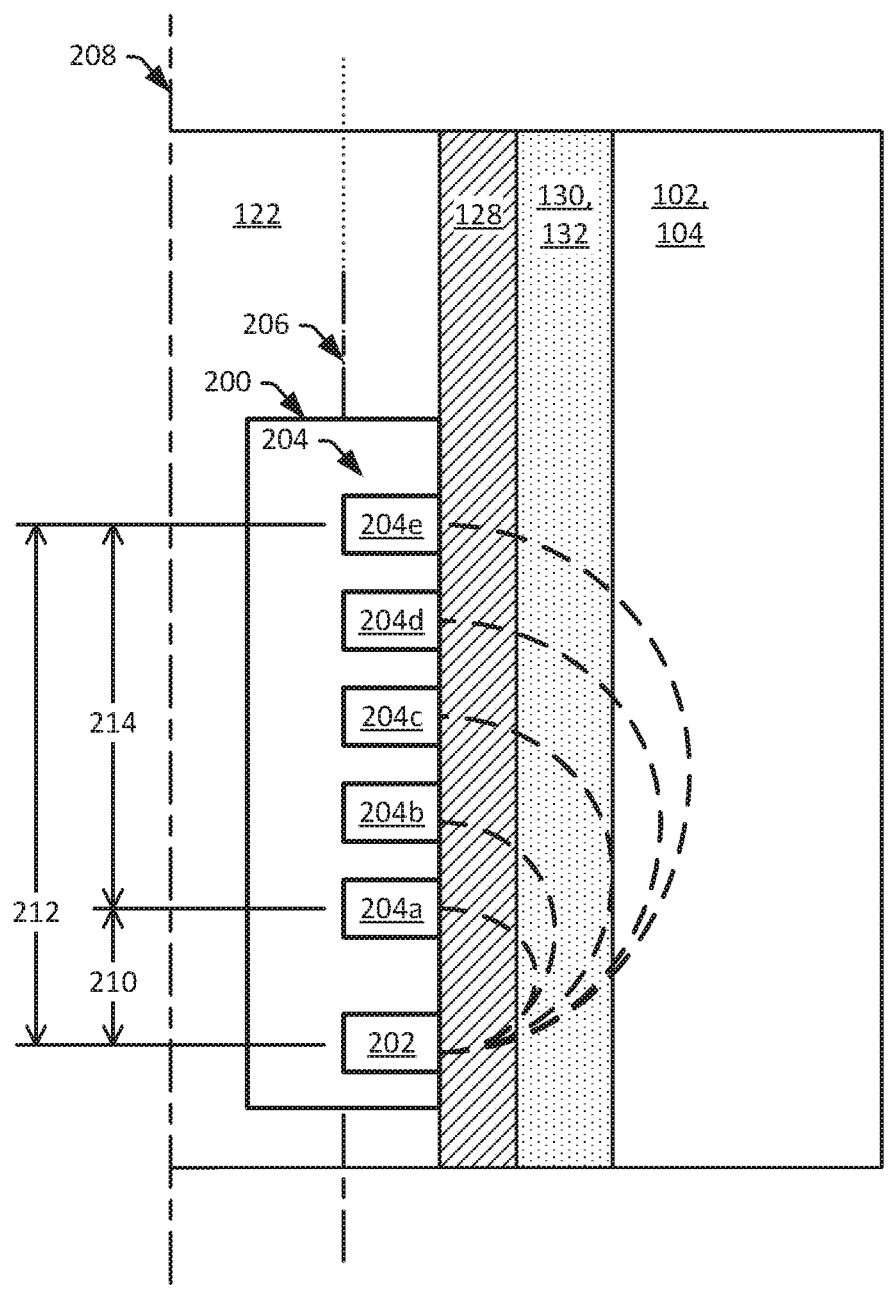
FIG. 2 is a diagram that illustrates a multi-detector (MD) pulsed neutron (PN) logging tool in accordance with one or more embodiments.

FIG. 2 is a diagram that illustrates an example MD PN logging tool 200 in accordance with one or more embodiments. In the illustrated embodiment, the MD PN logging tool 200 is configured to be disposed in the wellbore 122 of the well 120 during a PN logging operation to generate corresponding log data 146. In some embodiments, the MD PN logging tool includes a PN source 202 and multiple PN detectors 204 (e.g., detectors 204a-204e). The multiple PN detectors 204 may be spaced along a length of the PN logging tool 200 (e.g., spaced parallel to a longitudinal axis 206 of the PN logging tool 200). When lowered into the wellbore 122, the PN logging tool 200 may be disposed adjacent an interior wall/surface of the casing 128 with the tool longitudinal axis 206 generally parallel to a longitudinal axis 208 of the wellbore 122 such that each of the PN detectors 204 is adjacent a corresponding portion of the casing 128, the cement 130, the CBA 132, the reservoir and/or the formation 104.

In some embodiments, a first of the PN detectors 204 (e.g., PN detector 204a located nearest the PN source 202) is located a distance 210 from the PN source 202, a last of the PN detectors 204 (e.g., PN detector 204e located farthest the PN source 202) is located a distance 212 (greater than the distance 210) from the source 202 and/or a distance 214 from the first of the PN detectors 204 (e.g., from the PN detector 204a), and the detectors 204 are spaced across the distance 214. In some embodiments, the locations and/or spacing of the detectors 204 are adjusted to correspond to measurement objectives as described, for example, in U.S. Patent Publication No. 2015/0369956, which is hereby incorporated by reference in its entirety.

In some embodiments, each of the PN detector 204. has a corresponding volume of investigation (VOI) or depth of investigation (DOI) that includes the portions of the casing 128, the cement 130, the CBA 132, the reservoir and/or the formation 104 adjacent the PN detector. The VOI or DOI for a given PN detector may correspond to a path of neutron and gamma rays between the PN source 202 and the PN detector 204. The VOIs and the DOIs for each of the detectors 204a, 204b, 204c, 204d and 204e may, for example, correspond to the volume/depth of the dashed lines that illustrate example paths of neutron and gamma rays between the PN source 202 and the respective PN detectors 204a, 204b, 204c, 204d and 204e. In general, because cement 130 is located relatively close to the PN logging tool 200, a PN detector 204 located farther from the PN source 202 (e.g., having a VOI and DOI that extends relatively far from the PN logging tool 200) is less effected by the cement 130 than a PN detector 204 located nearer to the PN source 202 (e.g., having a VOI and DOI that is relatively close to the PN logging tool 200). Thus, the cement 130 within a detectors' VOI or DOI may have a greater effect on measurements by PN detectors 204 near the PN source 202 (e.g., the cement 130 may have the greatest effect on measurements by the PN detector 204a), and the cement 130 may have a lesser effect on measurements by PN detectors 204 farther from the PN source 202 (e.g., the cement 130 may have the least effect on measurements by the PN detector 204e).

In some embodiments, a carbon to oxygen ratio (C/O) is obtained via a PN logging operation of the well 120, and the C/O can be used to assess the quality of the cement 130 in the CBA 132 of the well 120. Based on simulations of C/O measured for wells, the following can be determined: (a) C/O decreases with the presence of water in the CBA of a well; (b) C/O increases with the presence of oil in the CBA of a well; (c) the effect of oil in the CBA on the C/O for a well is more profound than the effect of water in the CBA on the C/O for a well; (d) the effects of fluid in the CBA on the C/O is greater for lesser cement quality; and (e) the effects of fluid in the CBA are greater on measurements by PN detectors closer to a PN source, and lesser on measurements by PN detectors farther from the PN source. Such determinations may be true for various types of wells, including limestone and dolomite reservoirs, and wellbores that contain oil.

Figures 3, 4:
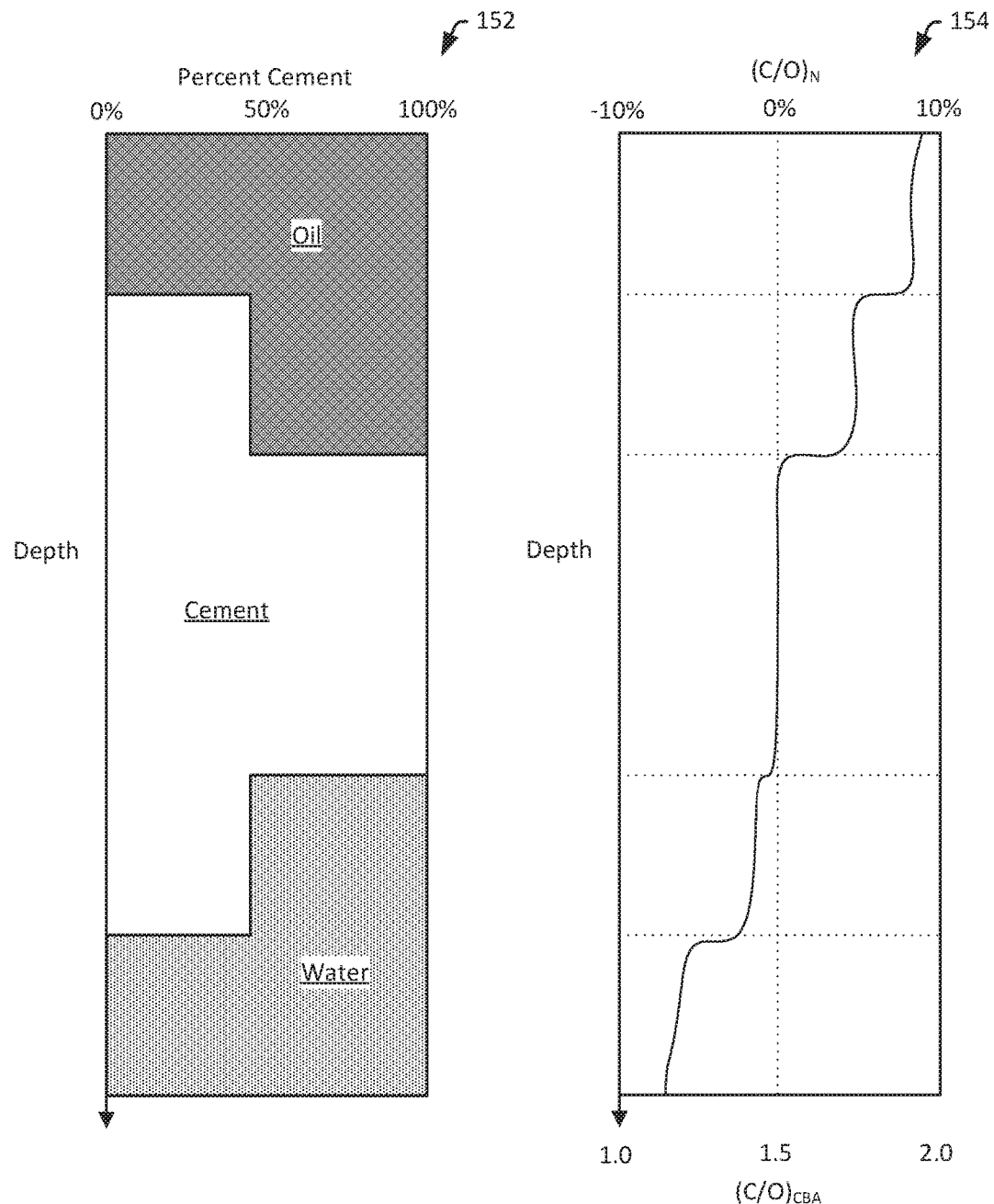
FIG. 3 is a diagram that illustrates a cement quality log (CQL) in accordance with one or more embodiments.
FIG. 4 is a diagram that illustrates a pulsed neutron (PN) log in accordance with one or more embodiments.

In some embodiments, a CBL for the well 120 is obtained and processed to determine a cement quality ($\Phi$) for the well 120. This can include conducting an initial CB logging operation for the well 120 shortly after casing the well 120 (e.g., conducting an initial CB logging operation less than 1 week after casing the well) to generate the CBL 150 for the well 120, and processing the CBL 150 to determine cement quality ($\Phi$) along a length of the well 120. Referring to FIG. 1, for example, conducting an initial CB logging operation shortly after casing the well 120 may include running a CB logging tool 144 in the wellbore 122 a few days after casing the well 120, and using the corresponding log data 146 to generate the CBL 150 for the well 120. Further, processing the CBL 150 to determine the cement quality ($\Phi$) along the length of the well 120 may include processing the CBL 150 to generate an initial CQL 152 that indicates presence of the cement 130 and/or voids filled with oil and/or water in the CBA 132 along the length of the well 120. FIG. 3 is a diagram that illustrates an example initial CQL 152 in accordance with one or more embodiments. The example CQL 152 indicates that a top section of the wellbore 122 has 100% oil (and 0% cement) in the CBA 132, an upper section of the wellbore 122 has 50% cement and 50% oil in the CBA 132, a midsection of the wellbore 122 has 100% cement (and 0% oil/water) in the CBA 132, a lower section of the wellbore 122 has 50% cement and 50% water in the CBA 132, and a bottom section of the of the wellbore 122 has 100% water (and 0% cement) in the CBA 132.

In some embodiments, using a carbon-oxygen ratio (C/O) for 100% cement as a reference, a normalized carbon-oxygen ratio can be determined as follows:

$$\left(\frac{C}{O}\right)_N = \frac{\left(\frac{C}{O}\right)_{meas} - \left(\frac{C}{O}\right)_{CBA=cmt}}{\left(\frac{C}{O}\right)_{CBA-cmt}} \quad (1)$$

where $(C/O)_N$ is the normalized carbon-oxygen ratio, $(C/O)_{meas}$ is the measured carbon-oxygen ratio at a given depth, and $(C/O)_{CBA=cmt}$ is the carbon-oxygen ratio when the CBA 132 is filled with 100% cement. If CBA is 100% filled with cement, $(C/O)_{meas}=(C/O)_{CBA=cmt}$, thus $(C/O)_N=0$. $(C/O)_{CBA=cmt}$ may be determined from the CBL 150, to have 100% cement. The relationship between $(C/O)_N$ and $(C/O)_{meas}$ may be considered as noise in traditional instances where PN measurements of $(C/O)_{meas}$ are used for well saturation monitoring, but, as explained herein, may be a useful signal for cement quality characterization, especially $(C/O)_N$ from detectors closer to the source, that carries more information of wellbore and near wellbore.

In some embodiments, a first/initial PNL for a well is obtained and processed to determine a first set of carbon-oxygen ratios (C/O) for the well. This can include conducting a first PN logging operation shortly after casing the well 120 (e.g., conducting a first PN logging operation less than 1 week after casing the well and/or within a few days of obtaining the CBL 150) to generate the first PNL 154 for the well 120. Thus, the first PN logging operation and the CB logging operation may both be conducted at a time when mud effects for the well are present. The first PNL 154 may be indicative of an initial C/O and or $(C/O)_N$ along a length of the wellbore 122 of the well 120 at the time of the first PN logging operation. FIG. 4 is a diagram that illustrates an example first PNL 154 in accordance with one or more embodiments. Notably, the CQL 152 and the PNL 154 may represent the same or similar length (or depth interval) of the wellbore 122. The example first PNL 154 indicates that the top section of the wellbore 122 has a C/O of about 1.9 (that corresponds to 100% oil and 0% cement in the CBA 132), the upper section of the wellbore 122 has a C/O of about 1.7 (that corresponds to 50% cement and 50% oil in the CBA 132), the midsection of the wellbore 122 has a C/O of about 1.5 (that corresponds to 100% cement and 0% oil/water in the CBA 132), the lower section of the wellbore 122 has a C/O of about 1.4 (that corresponds to 50% cement and 50% water in the CBA 132), and the bottom section of the of the wellbore 122 has a C/O of about 1.2 (that corresponds to 100% water and 0% cement in the CBA 132).

In some embodiments, a cement quality (Φ) can be determined based on maximum and minimum $(C/O)_N$ values. The cement quality (Φ) may be indicative of void spaces in the cement 130, beyond the void spaces attributable to the porosity of the cement 130. For example, where a CBL for a well indicates that water is present in a portion of the CBA of the wellbore of the well at a given depth, the cement quality for the portion of the CBA at the depth can be determined as follows:

$$\Phi_w = \frac{\left(\frac{C}{O}\right)_N}{\left(\frac{C}{O}\right)_{N,min}} \quad (2)$$

where $\Phi_w$ is "water" cement quality at the corresponding depth, $(C/O)_N$ is the normalized carbon-oxygen ratio at the depth, and $(C/O)_{N,min}$ is minimum carbon-oxygen ratio (e.g., −7%) for the CBA measured across the length of the wellbore logged by the CBL and/or the PNL. Referring to the portions of the CQL 152 and the PNL 154 that represent a portion of the bottom section of the wellbore 122 having 100% water (and 0% cement) in the CBA 132 and a $(C/O)_N$ of about −7%, a water cement quality ($\Phi_w$) for that portion of the CBA 132 may be determined to be about 100% (e.g., −7%/−7%=1.00). Referring to the portions of the CQL 152 and the PNL 154 that represent a portion of the lower section of the wellbore 122 having 50% cement and 50% water in the CBA 132 and a $(C/O)_N$ of about −2%, the water cement quality ($\Phi_w$) for that portion of the CBA 132 may be determined to be about 26% (e.g., −2%/−7%=0.26).

Where a CBL for a well indicates that oil is present in a portion of a CBA of a wellbore of the well at a given depth, the cement quality for the portion of the CBA at the depth can be determined as follows:

$$\Phi_w = \frac{\left(\frac{C}{O}\right)_N}{\left(\frac{C}{O}\right)_{N,max}} \quad (3)$$

where $\Phi_o$ is "oil" cement quality at the corresponding depth, $(C/O)_N$ is the normalized carbon-oxygen ratio at the depth, and $(C/O)_{N,max}$ is a maximum carbon-oxygen ratio (e.g., 9%) for the CBA measured across the length of the wellbore logged by the CBL and/or the PNL. Referring to the corresponding portions of the CQL 152 and the PNL 154 that represent a portion of the top section of the wellbore 122 having 100% oil (and 0% cement) in the CBA 132 and a $(C/O)_N$ of about 9%, an oil cement quality ($\Phi_o$) for that portion of the CBA 132 may be determined to be about 100% (e.g., 9%/9%=1.00). Referring to the portions of the CQL 152 and the PNL 154 that represent a portion of the upper section of the wellbore 122 having 50% cement and 50% oil in the CBA 132 and a $(C/O)_N$ of about 5%, an oil cement quality ($\Phi_o$) for that portion of the CBA 132 may be determined to be about 56% (e.g., 5%/9%=0.56). Accordingly, initial cement qualities (e.g., including water cement quality ($\Phi_w$) and oil cement qualities ($\Phi_o$)) can be determined based on the cement qualities (Φ) for locations in the CBA 132 indicated by the CBL 150 (and/or the CQL 152) and the corresponding normalized carbon-oxygen ratios $(C/O)_N$ determined from the first PNL 154.

Figure 5:
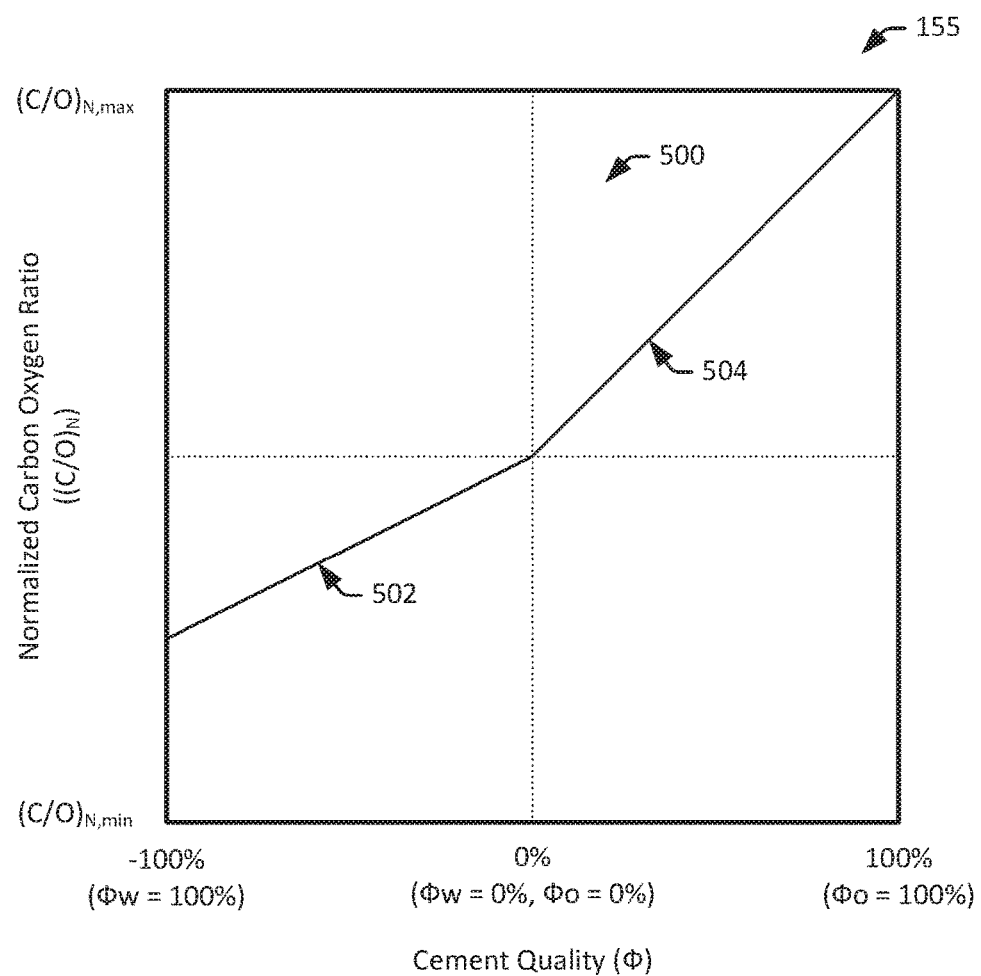
FIG. 5 is a diagram that illustrates a cement quality index (CQI) in accordance with one or more embodiments.

In some embodiments, a first PNL for a well is calibrated with a CQL for the well to generate a first/initial baseline CQI for the well. This can include cross-plotting the initial $(C/O)_N$ values of a first/initial PNL versus the initial cement quality values (e.g., including water cement quality ($\Phi_w$) values and oil cement qualities ($\Phi_o$) values). Thus, the CQI for the well may include a mapping of cement qualities to normalized carbon-oxygen ratios. FIG. 5 is a diagram that illustrates an example first baseline CQI 155 for the well 120 in accordance with one or more embodiments. The first baseline CQI 155 may include a cross-plot 500 of the initial $(C/O)_N$ values of the first PNL 154 versus the cement quality (Φ) values determined. Notably, the cement quality (Φ) may include the water cement quality ($\Phi_w$) extending to the left of the plot (consistent with "negative" values associated with $(C/O)_N$ where water is present), and the oil cement quality ($\Phi_o$) extending to the right of the plot (consistent with "positive" values associated with $(C/O)_N$ where oil is present). Referring to the above example cement quality (Φ) values, the cross-plot 500 may include a plot of at least the points ($\Phi_w$=100%, $(C/O)_N$=−7%), ($\Phi_w$=26%, $(C/O)_N$=−2%), ($\Phi_o$=100%, $(C/O)_N$=9%), ($\Phi_o$=56%, $(C/O)_N$=5%). Corresponding curves may be generated for the portion of the cross-plot 500 associated with negative and positive values of $(C/O)_N$, respectively. For example, a first curve 502 (e.g., a first best fit line) for at least the points ($\Phi_w$=100%, $(C/O)_N$=−7%) and ($\Phi_w$=26%, $(C/O)_N$=−2%) may be generated to represent the percentage of voids in the cement 130 filled with water when $(C/O)_N$ has a negative value, and a second curve 504 (e.g., a second best fit line) for at least the points ($\Phi_o$=100%, $(C/O)_N$=9%), ($\Phi_o$=56%, $(C/O)_N$=5%) may be generated to represent the percentage of voids in the cement 130 filled with oil when $(C/O)_N$ has a positive value. The cross-plot 500 may extend from a first cement quality (e.g., $\Phi_w$=100%, that corresponds to 100% water and 0% cement in the CBA 132), to a second cement quality ($\Phi_o$=100%, that corresponds to 100% oil and 0% cement in the CBA 132). The cross-plot 500 may extend from a minimum to a maximum $(C/O)_N$ (e.g., from $(C/O)_{N,min}$=−7% to $(C/O)_N$ $(C/O)_{N,max}$=9%).

Notably, if a $(C/O)_N$ for a location has a value of about zero, it can be determined that the cement quality remains good for that location. That is, the cement at that location does not have voids penetrated by water or oil. If a $(C/O)_N$ for a location has a value that is negative, it can be determined that the cement quality is deteriorated for that location, and/or the cement at that location has voids penetrated by water. A large negative value may indicate more severe deterioration of the cement, including a relatively large amount of void space filled by water. If a $(C/O)_N$ for a location has a value that is positive, it can be determined that the cement quality is deteriorated for that location, and/or the cement at that location has voids penetrated by oil. A large positive value may indicate more severe deterioration of the cement, including a relatively large amount of void space filled by oil. Thus, monitoring of the $(C/O)_N$ across the length of the wellbore of a well over a period of time can provide insight into the integrity of the cement in the CBA of the well over at least that period of time.

In some embodiments, a second PNL for a well is obtained and processed to determine a second set of carbon-oxygen ratios (C/O) for the well. This can include conducting a second PN logging operation for the well sometime after the first PN logging operation to generate the second PNL for the well. For example, a well may be subject to mud effects shortly after casing the well, and these mud effect may dissipate over time. In some instances, the mud effects may be reduced or eliminated after a given duration of time and/or after the well is perforated and/or production and/or injection operations commence. In some embodiments, the second PN logging operation for the well is conducted after it has been determined that the mud effects for the well have been reduced or eliminated. For example, a second PN logging operation for the well 120 may be conducted in response to determining that the mud effects (e.g., mud filtrate invasion) for the well 120 have been reduced or eliminated by a sufficient amount. In some embodiments, the determination may include determining that one or more triggering events have occurred. These events can include, for example, at least a threshold amount of time (e.g., 1 or more years, such as 1, 2, 3, 4, 5, 6, 7, 8 or more years) has passed since drilling and/or casing the well 120, a perforation operation for the well 120 has commenced and/or has been ongoing for at least a threshold amount of time (e.g., 1 or more months, such as 1, 2, 3, 4, 5, 6, 7, 8, 9, 10, 11, 12 or more months), a production operation for the well 120 has commenced and/or has been ongoing for at least a threshold amount of time (e.g., 1 or more months, such as 1, 2, 3, 4, 5, 6, 7, 8, 9, 10, 11, 12 or more months), and/or an injection operation for the well 120 has commenced and/or has been ongoing for at least a threshold amount of time (e.g., 1 or more months, such as 1, 2, 3, 4, 5, 6, 7, 8, 9, 10, 11, 12 or more months). In some embodiments, the determination of the reduction or elimination of the mud effects for a depth interval of the wellbore under investigation is based on the reservoir rock properties, a recipe or type of the mud used in the wellbore, and/or characteristics of the drilling operation (e.g., how much overbalance was adopted while drilling the interval of the wellbore under investigation). For example, where a relatively high overbalance was used for drilling of a depth interval of a well, it may be determined that the mud effects are dissipated after a relatively long period of time (e.g., 3 or more years after drilling and/or casing the depth interval of the well, 3 or more months after commencing a perforation operation, a production operation, and/or an injection operation at the depth interval of the well, and/or after a perforation operation, a production operation, and/or an injection operation at the depth interval has been ongoing for 3 or more months), and where a relatively low overbalance was used for drilling of a depth interval of a well, it may be determined that the mud effects are dissipated after a relatively short period of time (e.g., less than 3 years (e.g., 1-3 years) after drilling and/or casing the depth interval of the well, less than 3 months (e.g., 1-3 months) after commencing a perforation operation, a production operation, and/or an injection operation at the depth interval of the well, and/or after a perforation operation, a production operation, and/or an injection operation at the depth interval has been ongoing for less than 3 months (e.g., 1-3 months)).

In some embodiments, a second PNL obtained via the second logging operation can be used in to generate a tuned CQI for the well 120. For example, the second PNL 156 may be processed in a manner similar to the processing of the first PNL 154 to determine a second set of measured carbon-oxygen ratios $(C/O)_{meas2}$, a second set of cement quality values (e.g., including a second set of water cement quality values ($\Phi_w$) and a second set of oil cement quality values ($\Phi_o$)), and/or a second baseline CQI 158 that corresponds to the second PNL 156. The differences between the first data corresponding to the first PNL 154 and the second data corresponding to the second PNL 156 may be attributed to the reduced mud effects, including mud filtrate dissipation. In some embodiments, a tuned baseline CQI 160 is generated based on the first baseline CQI ($CQI_1$) 155 and/or the second baseline CQI ($CQI_2$) 158. For example, the tuned baseline CQI 160 may be generated based on an average of the first baseline CQI 155 and the second baseline CQI 158. In some embodiments, the second baseline CQI 158 may be used as the tuned baseline CQI 160. Within this short time period, reservoir saturation can be assumed to be fairly constant and differences observed between the first baseline CQI ($CQI_1$) 155 and the second baseline CQI ($CQI_2$) 158 may be attribute to the dissipation of mud filtrate invasion. In such an embodiment, the second baseline CQI ($CQI_2$) 158 can be considered more representative of CQI 160 than the first baseline CQI ($CQI_1$) 155, since the first baseline CQI ($CQI_1$) 155 mud filtrate invasion has a greater effect on the first baseline CQI ($CQI_1$) 155 than the second baseline CQI ($CQI_2$) 158. Consistent with this, in some embodiments, the second baseline CQI ($CQI_2$) 158 is more heavily weighted than the first baseline CQI ($CQI_1$) 155 in a determination of the tuned baseline CQI 160. For example, the tuned baseline CQI 160 may be determined as follows, where X is a weighting having a value greater than 0.5 and less than or equal to 1:

$$CQI_{tuned} = \frac{((1-X)CQI_1) + ((X)CQI_2)}{2} \quad (4)$$

In some embodiments, the tuned CQI 160 may serve as the baseline against which future $(C/O)_N$ values are compared to determine a corresponding cement quality and whether the cement 132 remains good or deteriorating over time.

In some embodiments, follow-up PN logging operations are conducted for a well to generate one or more updated PNLs that can be used to assess the integrity of the well's cement over time and/or water saturation for the well. In some embodiments, follow-up PN logging operations is conducted in the normal course of well operations to assess cement quality, water saturation and/or the like. For example, where PN logging operations are conducted on a monthly basis for the well 120, a third PN logging operation may be conducted one month after the second PN logging operation to generate a third PNL 162, a fourth PN logging operation may be conducted two months after the second PN logging operation to generate a fourth PNL 162, and so forth. Thus, the cement quality can continually be assessed in the course of normal well operations, including PN logging operations. Thus, special operations, such as pulling the production components via a workover rig to conduct a CB logging operation, may not need to be undertaken to assess and monitor the cement quality.

In some embodiments, follow-up PNL generated from a follow-up PN logging operation is used to assess the cement quality for the well. The follow-up PNL may include an updated set of measured carbon-oxygen ratios $(C/O)_{CBA}$ and a corresponding set of $(C/O)_N$ values. In some embodiments, the tuned baseline CQI 160 can be used to determine updated cement quality values for the well at the time of a follow-up PN logging operation. For example, where a third PNL 162 indicates a $(C/O)_N$ value of about −2% at a depth of 1000 meters (m) in the wellbore 122 of the well 120, and the cross-plot 500 of the tuned CQI 160 includes a first curve 502 having a point of ($\Phi_w$=26%, $(C/O)_N$=−2%), a lookup operation can be conducted using the cross-plot 500 of the tuned CQI 160 to determine a cement quality value of $\Phi_w$=26% for the CBA 132 at the depth of 1000 m. Such a determination can be repeated for various depths in the wellbore 122 to generate an updated CQL 164 for the well 120. For example, where the third PNL 162 indicates a $(C/O)_N$ value of about 0% at a depth of 1500 m in the wellbore 122, and the cross-plot 500 of the tuned baseline CQI 154c includes a first curve 502 having a point of ($\Phi_w$=0%, $(C/O)_N$=0%) and/or a second curve 504 having a point of ($\Phi_o$=0%, $(C/O)_N$=0%), a lookup operation can be conducted using the cross-plot 500 of the tuned CQI 160 to determine a cement quality value of $\Phi_w$=0% and/or $\Phi_o$=0% for the CBA 132 at the depth of 1500 m. As a further example, where the third PNL 162 indicates a $(C/O)_N$ value of about 5% at a depth of 2000 m in the wellbore 122 of the well 120, and the cross-plot 500 of the tuned baseline CQI 154c includes a second curve 504 having a point of ($\Phi_o$=56%, $(C/O)_N$=5%), then a lookup operation can be conducted using the cross-plot 500 of the tuned baseline CQI 154c to determine a cement quality value of $\Phi_o$=56% for the CBA 132 at the depth of 2000 m.

In some embodiments, cement quality values determined from follow-up PNLs can be used to determine a condition of the corresponding portion of the cement in the CBA of the well. For example, it can be determined that the portion of CBA 132 at a depth of 1000 m has deteriorated cement 130 with voids that are filled with water based on the determined cement quality value of $\Phi_w$=26%; it can be determined that the portion of CBA 132 at a depth of 1500 m has cement 130 in relatively good condition (e.g., it does not have voids penetrated by water or oil) based on the determined cement quality value of $\Phi_w$=0% and/or $\Phi_o$=0%; and/or it can be determined that the portion of CBA 132 at a depth of 2000 m has deteriorated cement 130 with voids that are filled with oil based on the determined cement quality value of $\Phi_o$=56%. In some embodiments, an updated CQL can be generated based on the data obtained via the a follow-up PNL to indicate the determined cement quality values along the corresponding length of a well. For example, an updated CQL 164 may be generated that includes a plot of the determined cement quality values vs depth, based on the third PNL 162. Thus, the updated CQL 164 may be based on a recently conducted follow-up PN logging operation, as opposed to the CBL 150 derived from the initial CB logging operation conducted shortly after casing the well 120.

In some embodiments, the cement quality values determined from a follow-up PNL can be compared to cement quality values determined from a prior PNL obtained via a prior PN logging operation to determine whether the condition of the cement is deteriorating or otherwise changing. For example, if a the second PNL 156 is used to determine a cement quality value of $\Phi_w$=0% and/or $\Phi_o$=0% for the depth of 1500 m in the wellbore 122 of the well 120, and the third PNL 162 is used to determine a cement quality value of $\Phi_w$=0% and/or $\Phi_o$=0% for the depth of 1500 m in the wellbore 122 of the well 120, then it may be determined that the cement 130 at 1500 m remains in good condition and has not deteriorated over the period of time from the second PN logging operation to the third PN logging operation. If, however, a fourth PNL 162 (acquired via a fourth PN logging operation) is used to determine a cement quality value of $\Phi_o$=56% for the depth of 1500 m in the wellbore 122 of the well 120, it may be determined that the cement 130 at 1500 m has deteriorated to a condition that includes voids that are filled with oil. Similar comparisons can be made for different depths over time to determine trends in the integrity of the cement 130 in the CBA 132 of the wellbore 122 of the well 120. In some embodiments, the cement quality values can be used to monitor well integrity, including the flow of fluids behind casing pipes and the spread of the flow over time.

In some embodiments, a remediation operation can be conducted to address relatively low cement qualities. For example, a cement remediation operation may be conducted to improve the quality of the cement 130 in a location (e.g., at a given depth in the CBA 132) in response to determining that the cement 130 at the location is associated with a cement quality value above a cement quality threshold (e.g., a $\Phi_w$>50% and/or a $\Phi_o$>50%). In some embodiments, a remediation operation includes a remedial squeeze operation, a re-cementing operation and/or the like to improve the quality of the cement 130 at the location. This can be of increased importance where, for example, the location requires cement to isolate fluids and/or pressures of different zones of the wellbore and/or the reservoir.

In some embodiments, the determined cement qualities are used to improve the accuracy of water saturation logs. For example, where a PN logging operation is conducted to generate a follow-up PNL 162, the follow-up PNL 162 can be used to generate an adjusted $S_w$ log for the well 120 and/or an updated CQL 164 for the well. The $S_w$ log may include an initial series of saturation values vs depth over a given interval determined from the log data 146 of the follow-up PN logging operations. The updated CQL 164 may include a corresponding series of cement quality values vs depth over the given interval. A tool characterization can be prepared that includes an indication of cement quality vs saturation. The saturation values of the $S_w$ log for each depth may be adjusted based on the corresponding cement quality values of the CQL 164, to generate an updated/adjusted and more accurate $S_w$ log 166 that accounts for the determined cement quality values. Changes of $S_w$ as a result of cement quality can be based on tool cement quality characterization, via laboratory measurements and/or simulation. Thus, an improved $S_w$ log that accounts for cement quality can be generated from a follow-up PN logging operation.

Figure 6:
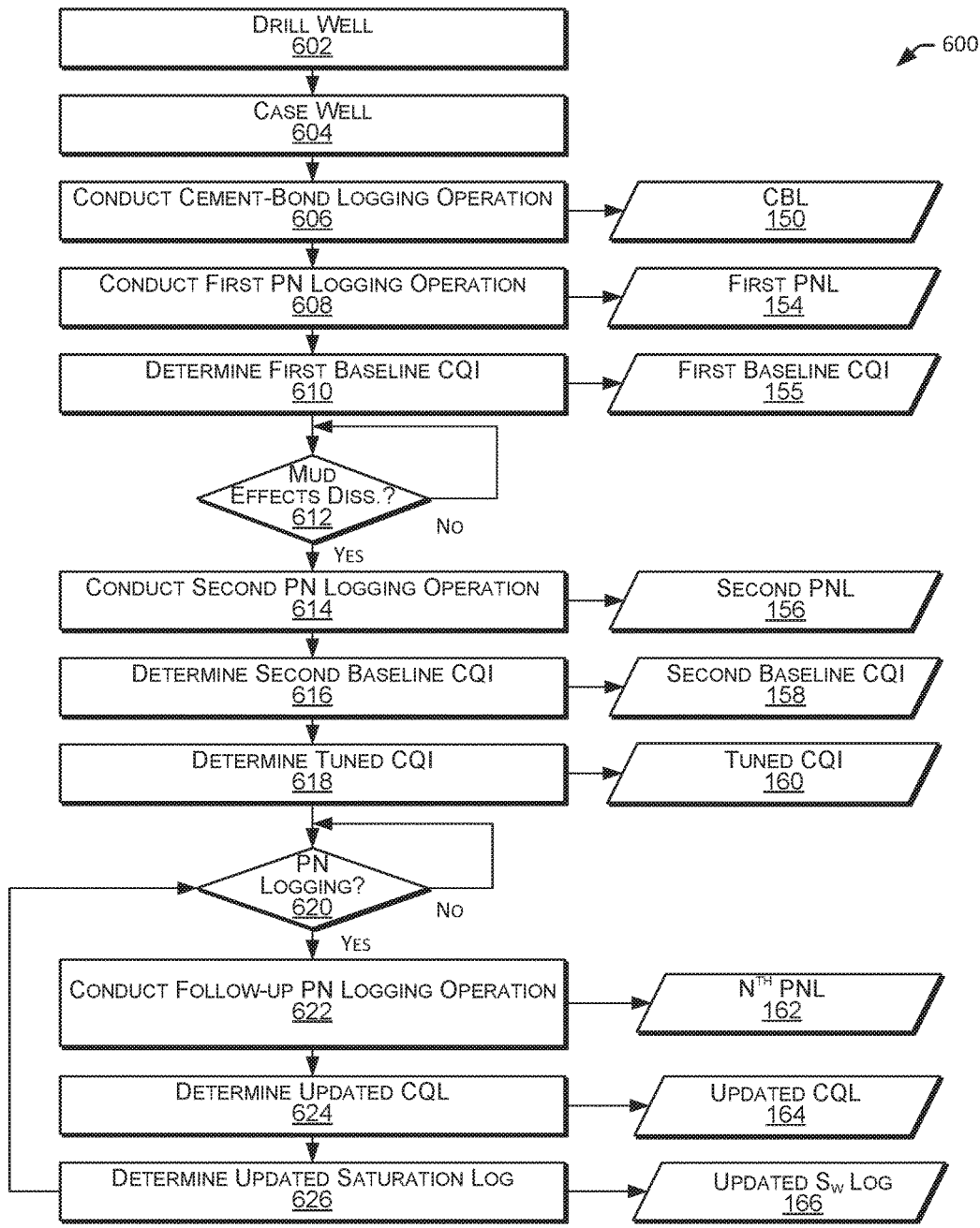
FIG. 6 is a flowchart that illustrates a method for monitoring a well in accordance with one or more embodiments.

FIG. 6 is a flowchart that illustrates a method 600 for monitoring a well in accordance with one or more embodiments. Method 600 generally includes drilling a well (block 602), casing the well (block 604), conducting a CB logging operation (block 606), conducting a first PN logging operation (block 608), determining a first baseline CQI (block 610), determine whether mud effects have dissipated (block 612), in response to determine that mud effects have dissipated, conducting a second PN logging operation (block 614), determining a second baseline CQI (block 616), determining a tuned CQI (block 618), determining whether a PN logging operation is needed (block 620), in response to determining that PN logging is needed conducting a follow-up PN logging operation (block 622), determining an updated CQL (block 624), and determining an updated $S_w$ log (block 626). In some embodiments, some or all of the operations of method 600 may be performed and/or controlled by the WAC system 140.

In some embodiments, drilling a well (block 602) includes drilling a wellbore of a well into a subsurface reservoir. For example, drilling a well may include the well controller 142 controlling a drilling operating to drill the wellbore 122 into the formation 104 and the reservoir 102.

In some embodiments, casing the well (block 604) includes conducting a casing operation to install casing in the wellbore of the well. For example, casing the well may include the well controller 142 controlling a setting operation to set the casing 128 in the wellbore 122, and controlling a cementing operation to dispose the cement 130 in the CBA 132.

In some embodiments, conducting a CB logging operation (block 606) includes conducting a CB logging operation that includes disposing a CB logging tool in the wellbore of the well to generate a corresponding CBL. For example, conducting a CB logging operation may include the well controller 142 controlling a CB logging operation that includes lowering a CB logging tool in the casing 128 and across a length of the wellbore 122, operating the CB logging tool to emit acoustic waves (e.g., ultrasonic waves) that propagate into the casing 128, the cement 130 and/or the formation 104 and to measure resulting acoustic waves, obtaining log data 146 that corresponds to the measurements by the CB logging tool, and generating a corresponding CBL 150 (and/or a corresponding initial CQL 152).

In some embodiments, conducting a first PN logging operation (block 608) includes conducting a PN logging operation that includes disposing a PN logging tool in the wellbore of the well to generate a corresponding first PNL. For example, conducting a first PN logging operation may include the well controller 142 controlling a first PN logging operation that includes lowering a MD PN logging tool into the casing 128 and across a length of the wellbore 122, operating the MD PN logging tool to emit bursts of high energy neutrons that are absorbed by nuclei in the formation 104 and to measure gamma rays output by the nuclei as a result of absorbing the neutrons, obtaining log data 146 that corresponds to the measurements by the PN logging tool, and generating a corresponding first PNL 154.

In some embodiments, determining a first baseline CQI (block 610) includes determining a baseline CQI for the well based on the CBL and the first PNL for the well. For example, determining a first baseline CQI may include the well controller 142 generating a first baseline CQI 155 based on the CBL 150, the CQL 152, and/or the first PNL 154. In some embodiments, the first baseline CQI 155 includes a cross-plot 500 of the initial $(C/O)_N$ values of the first PNL 154 versus the cement quality ($\Phi$) values determined from the CBL 150 and/or the CQL 152. The first baseline CQI 155 may include a first mapping of cement qualities to normalized carbon-oxygen ratios. Thus, determining a first baseline CQI may include calibrating the first PNL 154 with the CBL 150 and/or the CQL 152.

In some embodiments, determining whether mud effects have dissipated (block 612) includes determining whether mud effects for the well (e.g., present at the time of the CB logging operation of the CB logging operation and/or the first PN logging operation) have been reduced or eliminated by a sufficient amount. For example, determining whether mud effects have dissipated may include the well controller 142 determining whether one or more triggering events have occurred. These events can include, for example, at least a given amount of time (e.g., 1 or more years, such as 1, 2, 3, 4, 5, 6, 7, 8 or more years) has passed since drilling and/or casing the well 120, a perforation operation for the well 120 has commenced and/or has been ongoing for at least a given amount of time (e.g., 1 or more months, such as 1, 2, 3, 4, 5, 6, 7, 8, 9, 10, 11, 12 or more months), a production operation for the well 120 has commenced and/or has been ongoing for at least a given amount of time (e.g., 1 or more months, such as 1, 2, 3, 4, 5, 6, 7, 8, 9, 10, 11, 12 or more months), and/or an injection operation for the well 120 has commenced and/or has been ongoing for at least a given amount of time (e.g., 1 or more months, such as 1, 2, 3, 4, 5, 6, 7, 8, 9, 10, 11, 12 or more months). In some embodiments, the determination of the reduction or elimination of the mud effects for a depth interval of the wellbore under investigation is based on the reservoir rock properties, a recipe or type of the mud used in the wellbore, and/or characteristics of the drilling operation (e.g., how much overbalance was adopted while drilling the interval of the wellbore under investigation). For example, where a relatively high overbalance was used for drilling of a depth interval of a well, it may be determined that the mud effects are dissipated after a relatively long period of time (e.g., 3 or more years after drilling and/or casing the depth interval of the well, 3 or more months after commencing a perforation operation, a production operation, and/or an injection operation at the depth interval of the well, and/or after a perforation operation, a production operation, and/or an injection operation at the depth interval has been ongoing for 3 or more months), and where a relatively low overbalance was used for drilling of a depth interval of a well, it may be determined that the mud effects are dissipated after a relatively short period of time (e.g., less than 3 years (e.g., 1-3 years) after drilling and/or casing the depth interval of the well, less than 3 months (e.g., 1-3 months) after commencing a perforation operation, a production operation, and/or an injection operation at the depth interval of the well, and/or after a perforation operation, a production operation, and/or an injection operation at the depth interval has been ongoing for less than 3 months (e.g., 1-3 months)).

In some embodiments, conducting a second PN logging operation (block 614) includes conducting a second PN logging operation that includes disposing a PN logging tool in the wellbore of the well to generate a corresponding second PNL. For example, conducting a second PN logging operation may include the well controller 142 controlling a second PN logging operation that includes lowering a PN logging tool into the casing 128 and across a length of the wellbore 122, operating the PN logging tool to emit bursts of high energy neutrons that are absorbed by nuclei in the formation 104 and to measure gamma rays output by the nuclei as a result of absorbing the neutrons, obtaining log data 146 that corresponds to the measurements by the PN logging tool, and generating a corresponding second PNL 156.

In some embodiments, determining a second baseline CQI (block 616) includes determining a baseline CQI for the well based on the CBL and a second PNL for the well. For example, determining a second baseline CQI may include the well controller 142 generating a second baseline CQI 158 based on the CBL 150, the CQL 152, and/or the second PNL 156. In some embodiments, the second baseline CQI 158 may include a cross-plot 500 of the $(C/O)_N$ values of the second PNL 156 versus the cement quality ($\Phi$) values determined from the CBL 150 and/or the CQL 152. The second baseline CQI 158 may include a first mapping of cement qualities to normalized carbon-oxygen ratios. Thus, determining a second baseline CQI may include calibrating the second PNL 154 with the CBL 150 and/or the CQL 152.

In some embodiments, determining a tuned CQI (block 618) includes determining a tuned CQI for the well based on the first and/or the second baseline CQIs for the well. For example, determining a tuned CQI may include the well controller 142 generating a tuned CQI 160 based on the first baseline CQI 155 and/or the second baseline CQI 158. For example, the tuned baseline CQI 160 may be generated based on an average of the first baseline CQI 155 and the second baseline CQI 158. In some embodiments, the second baseline CQI 158 may be used as the tuned baseline CQI 160. The tuned baseline CQI 160 may include a third/tuned mapping of cement qualities to normalized carbon-oxygen ratios. Within this short time period, reservoir saturation can be assumed to be fairly constant and differences observed between the first baseline CQI ($CQI_1$) 155 and the second baseline CQI ($CQI_2$) 158 may be attribute to the dissipation of mud filtrate invasion. In such an embodiment, the second baseline CQI ($CQI_2$) 158 can be considered more representative of CQI 160 than the first baseline CQI ($CQI_1$) 155, since the first baseline CQI ($CQI_1$) 155 mud filtrate invasion has a greater effect on the first baseline CQI ($CQI_1$) 155 than the second baseline CQI ($CQI_2$) 158. Consistent with this, in some embodiments, the second baseline CQI ($CQI_2$) 158 is more heavily weighted than the first baseline CQI ($CQI_1$) 155 in a determination of the tuned baseline CQI 160. For example, the tuned baseline CQI 160 may be determined as provided in equation 4.

In some embodiments, determining whether a PN logging operation is needed (block 620) includes determining whether a follow-up PN logging operation is needed in the normal course of well operations. For example, where PN logging operations are conducted on a monthly basis for the well 120, the well controller 142 may determine that a third PN logging operation is needed about one month after the second PN logging operation, a fourth PN logging operation is needed about two months after the second PN logging operation, and so forth.

In some embodiments, conducting a follow-up PN logging operation (block 622) includes conducting a follow-up PN logging operation that includes disposing a PN logging tool in the wellbore of the well to generate a corresponding follow-up PNL. For example, conducting a third/follow-up PN logging operation may include the well controller 142 controlling a third PN logging operation that includes lowering a PN logging tool into the casing 128 and across a length of the wellbore 122, operating the PN logging tool to emit bursts of high energy neutrons that are absorbed by nuclei in the formation 104 and to measure gamma rays output by the nuclei as a result of absorbing the neutrons, obtaining log data 146 that corresponds to the measurements by the PN logging tool, and generating a corresponding third/follow-up PNL 162. In some embodiments, the follow-up PN logging operation is conducted without removing completion components (e.g., without removing production tubing) from the wellbore 122 of the well 120.

In some embodiments, determining an updated CQL (block 624) includes determining an updated CQL for the well based on the follow-up PNL. For example, determining an updated CQL may include the well controller 142 determining a corresponding cement quality value for each depth in the updated set of $(C/O)_N$ values of the third/follow-up PNL 162 (e.g., via a look-up operation) and generating an updated CQL 164 that includes a log of the cement quality values determined vs depth for the length of the wellbore 122. Thus, the updated CQL 164 may include a mapping of cement quality values versus depth in the wellbore 122.

In some embodiments, determining an updated $S_w$ log (block 626) includes determining an updated $S_w$ log for the well based on the updated CQL for the well and/or the follow-up PNL. For example, determining an updated $S_w$ log may include the well controller 142 determining an initial $S_w$ log for the well 120 based on the third/follow-up PNL 162 and adjusting the saturation values of the $S_w$ log based on the cement quality values of the CQL 164 to generate an adjusted/updated $S_w$ log 166. Changes of $S_w$ as a result of cement quality can be based on tool cement quality characterization via laboratory measurements and/or simulation. The resulting $S_w$ log can be used, for example, to determine the concentration of water and/or hydrocarbons at the various depth intervals along the length of the well 120. This information can be used to make various determinations regarding operating and characterizing the well 120. For example, where the $S_w$ log 166 indicates a relatively high water saturation along the cased interval/portion 124 of the wellbore 122 of the well 120, a follow-up completion operation can be conducted to seal-off nearby open-hole portions 126 of the wellbore 122 to prevent water breakthrough in the open-hole portions 126, thereby inhibiting the water for mixing with produced hydrocarbons flowing through the wellbore 122. In some embodiments, a production estimate for the well 120 can be adjusted lower to account for the realization that water is moving closer to the producing intervals (e.g., the open-hole portions 126) of the well 120. In some embodiments, enhanced recovery operations, such as injection operations can be conducting in an effort to inhibit the movement of the water in the formation 104 toward to the producing intervals (e.g., the open-hole portions 126) of the well 120.

Figure 7:
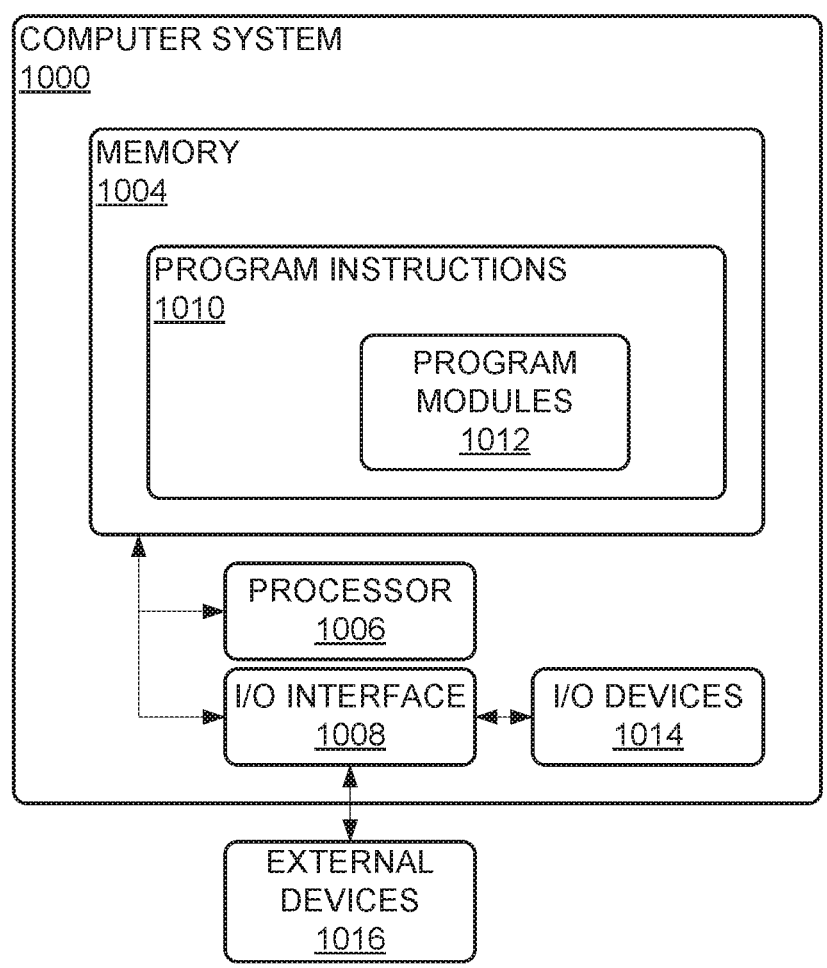
FIG. 7 is a diagram that illustrates an example computer system in accordance with one or more embodiments.

FIG. 7 is a diagram that illustrates an example computer/control system 1000 in accordance with one or more embodiments. In some embodiments, the system 1000 may be a programmable logic controller (PLC). The system 1000 may include a memory 1004, a processor 1006, and an input/output (I/O) interface 1008. The memory 1004 may include non-volatile memory (e.g., flash memory, read-only memory (ROM), programmable read-only memory (PROM), erasable programmable read-only memory (EPROM), electrically erasable programmable read-only memory (EEPROM)), volatile memory (e.g., random access memory (RAM), static random access memory (SRAM), synchronous dynamic RAM (SDRAM)), bulk storage memory (e.g., CD-ROM and/or DVD-ROM, hard drives), and/or the like. The memory 1004 may include a non-transitory computer-readable storage medium having program instructions 1010 stored therein. The program instructions 1010 may include program modules 1012 that are executable by a computer processor (e.g., the processor 1006) to cause the functional operations described herein, including the operations of the WAC system 140, the well controller 142, and/or the method 600.

The processor 1006 may be any suitable processor capable of executing/performing program instructions. The processor 1006 may include a central processing unit (CPU) that carries out program instructions (e.g., the program instructions of the program module(s) 1012) to perform the arithmetical, logical, and input/output operations described herein. The processor 2006 may include one or more processors. The I/O interface 1008 may provide an interface for communication with one or more I/O devices 1014, such as a joystick, a computer mouse, a keyboard, a display screen (e.g., an electronic display for displaying a graphical user interface (GUI)), and/or the like. The I/O devices 1014 may include one or more of the user input devices. The I/O devices 1014 may be connected to the I/O interface 1008 via a wired (e.g., Industrial Ethernet) or a wireless (e.g., Wi-Fi) connection. The I/O interface 1008 may provide an interface for communication with one or more external devices 1016, such as other computers, networks, and/or the like. In some embodiments, the I/O interface 1008 may include an antenna, a transceiver, and/or the like. In some embodiments, the external devices 1016 may include one or more logging tools, and/or the like.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as examples of embodiments. Elements and materials may be substituted for those illustrated and described herein, parts and processes may be reversed or omitted, and certain features of the embodiments may be utilized independently, all as would be apparent to one skilled in the art after having the benefit of this description of the embodiments. Changes may be made in the elements described herein without departing from the spirit and scope of the embodiments as described in the following claims. Headings used herein are for organizational purposes only and are not meant to be used to limit the scope of the description.

It will be appreciated that the processes and methods described herein are example embodiments of processes and methods that may be employed in accordance with the techniques described herein. The processes and methods may be modified to facilitate variations of their implementation and use. The order of the processes and methods and the operations provided therein may be changed, and various elements may be added, reordered, combined, omitted, modified, etc. Portions of the processes and methods may be implemented in software, hardware, or a combination thereof. Some or all of the portions of the processes and methods may be implemented by one or more of the processors/modules/applications described herein.

As used throughout this application, the word "may" is used in a permissive sense (i.e., meaning having the potential to), rather than the mandatory sense (i.e., meaning must). The words "include," "including," and "includes" mean including, but not limited to. As used throughout this application, the singular forms "a", "an," and "the" include plural referents unless the content clearly indicates otherwise. Thus, for example, reference to "an element" may include a combination of two or more elements. As used throughout this application, the phrase "based on" does not limit the associated operation to being solely based on a particular item. Thus, for example, processing "based on" data A may include processing based at least in part on data A and based at least in part on data B unless the content clearly indicates otherwise. As used throughout this application, the term "from" does not limit the associated operation to being directly from. Thus, for example, receiving an item "from" an entity may include receiving an item directly from the entity or indirectly from the entity (e.g., via an intermediary entity). Unless specifically stated otherwise, as apparent from the discussion, it is appreciated that throughout this specification discussions utilizing terms such as "processing," "computing," "calculating," "determining," or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical, electronic or magnetic quantities within memories, registers, or other information storage devices, transmission devices, or display devices of the special purpose computer or similar special purpose electronic processing/computing device.

What is claimed is:

1. A method for monitoring cement quality of a cased well, the method comprising:
conducting a cement-bond (CB) logging of a well to generate cement-bond log (CBL) for the well, the well comprising:
a wellbore penetrating a subsurface formation;
casing disposed in the wellbore; and
cement disposed in a casing-borehole annulus (CBA) located between the casing and the formation;
conducting a first pulsed neutron (PN) logging of the well to generate a first pulsed neutron log (PNL) for the well, the first PNL indicating carbon-oxygen ratios for the well at the time of the first PN logging;
determining a first baseline cement quality index (CQI) for the well based on the CBL and the first PNL, the first baseline CQI comprising a first mapping of cement qualities to normalized carbon-oxygen ratios;
determining that mud effects for the well present at the time of the first PN logging of the well have dissipated;
in response to determining that mud effects have dissipated, conducting a second PN logging of the well to generate a second PNL for the well, the second PNL indicating carbon-oxygen ratios for the well at the time of the second PN logging;

determining a second baseline CQI for the well based on the CBL and the second PNL, the second baseline CQI comprising a second mapping of cement qualities to normalized carbon-oxygen ratios;

determining a tuned CQI for the well based on the first baseline CQI and the second baseline CQI, the tuned CQI comprising a third mapping of cement qualities to normalized carbon-oxygen ratios;

conducting a follow-up PN logging of the well to generate a follow-up PNL for the well, the follow-up PNL indicating carbon-oxygen ratios for the well at the time of the follow-up PN logging; and determining an updated cement quality log (CQL) for the well based on the tuned CQI and the follow-up PNL, the updated CQL comprising a mapping of cement quality values versus depth in the wellbore.

2. The method of claim 1, further comprising determining an updated water saturation log for the well based on follow-up PNL.

3. The method of claim 2, wherein determining an updated water saturation ($S_w$) log for the well based on follow-up PNL comprises determining an initial $S_w$ log for the well based on the follow-up PNL, and adjusting water saturation values of the initial $S_w$ log based on corresponding cement quality values of the updated CQL to generate the updated $S_w$ log.

4. The method of claim 1, wherein the follow-up PN logging of the well is conducted without removing completion components from the wellbore of the well.

5. The method of claim 1, wherein determining that mud effects for the well present at the time of the first PN logging of the well have dissipated comprises determining that at least a threshold amount of time has passed since casing the well.

6. The method of claim 1, wherein determining that mud effects for the well present at the time of the first PN logging of the well have dissipated comprises determining that at least one year has passed since casing the well.

7. The method of claim 1, wherein determining that mud effects for the well present at the time of the first PN logging of the well have dissipated comprises determining that a perforation, a production or an injection operation for the well has been ongoing for at least a threshold amount of time.

8. The method of claim 1, wherein the first, second, and follow-up PN loggings of the well are conducted using a multi-detector (MD) PN logging tool.

9. The method of claim 8, wherein the MD PN tool comprises a single PN source and multiple PN detectors.

10. The method of claim 1, further comprising:
determining that a portion of the cement at a location is deteriorated based on the updated CQL; and
conducting a remediation operation to improve the quality of the cement in the location.

11. A method for monitoring cement quality of a cased well, the method comprising:
obtaining, by well controller system, a cement-bond log (CBL) for a well, the CBL obtained via a cement-bond logging of the well conducted after casing the well and when mud effects for the well are present, the well comprising:
a wellbore penetrating a subsurface formation;
casing disposed in the wellbore; and
cement disposed in a casing-borehole annulus (CBA) located between the casing and the formation;
obtaining, by the well control system, a first pulsed neutron log (PNL) for the well, the first PNL obtained via a first pulsed neutron (PN) logging of the well conducted after casing the well and at a time when mud effects for the well are present;

determining, by the well control system, a first baseline cement quality index (CQI) for the well based on the CBL and the first PNL, the first baseline CQI comprising a first mapping of cement qualities to normalized carbon-oxygen ratios;

obtaining, by the well control system, a second PNL for the well, the second PNL obtained via a second PN logging of the well conducted after casing the well, after the first PN logging of the well, and at a time when the mud effects for the well are not present;

determining, by the well control system, a second baseline CQI for the well based on the CBL and the second PNL, the second baseline CQI comprising a second mapping of cement qualities to normalized carbon-oxygen ratios;

determining, by the well control system, a tuned CQI for the well based on the first baseline CQI and the second baseline CQI, the tuned CQI comprising a third mapping of cement qualities to normalized carbon-oxygen ratios;

obtaining, by the well control system, a follow-up PNL for the well, the follow-up PNL obtained via a follow-up PN logging of the well conducted after the second PN logging of the well, the follow-up PNL indicating carbon-oxygen ratios for the well at the time of the follow-up PN logging of the well; and determining, by the well control system, an updated cement quality log (CQL) for the well based on the tuned CQI and the follow-up PNL for the well, the updated CQL comprising a mapping of cement quality values versus depth in the wellbore.

12. The method of claim 11, further comprising determining an updated water saturation ($S_w$) log for the well based on follow-up PNL.

13. The method of claim 12, wherein determining an updated $S_w$ log for the well based on follow-up PNL comprises determining an initial $S_w$ log for the well based on the follow-up PNL, and adjusting water saturation values of the initial $S_w$ log based on corresponding cement quality values of the updated CQL to generate the updated $S_w$ log.

14. The method of claim 11, wherein the follow-up PN logging of the well is conducted without removing completion components from the wellbore of the well.

15. The method of claim 11, wherein the second PN logging of the well is conducted at least a threshold amount of time after casing the well.

16. The method of claim 11, wherein the second PN logging of the well is conducted at least a one year after casing the well.

17. The method of claim 1, wherein the second PN logging of the well is conducted after a perforation, a production or an injection operation for the well has been ongoing for at least a threshold amount of time.

18. The method of claim 11, wherein the first, second, and follow-up PN loggings of the well are conducted using a multi-detector (MD) PN logging tool.

19. The method of claim 18, wherein the MD PN tool comprises a single PN source and multiple PN detectors.

20. A system for monitoring cement quality of a cased well, the system comprising:
a well control system configured to:
obtain a cement-bond log (CBL) for a well, the CBL obtained via a cement-bond (CB) logging of the well conducted after casing the well and when mud effects for the well are present, the well comprising:
a wellbore penetrating a subsurface formation;
casing disposed in the wellbore; and
cement disposed in a casing-borehole annulus (CBA) located between the casing and the formation;

obtain a first pulsed neutron log (PNL) for the well, the first PNL obtained via a first pulsed neutron (PN) logging of the well conducted after casing the well and at a time when mud effects for the well are present;

determine a first baseline cement quality index (CQI) for the well based on the CBL and the first PNL, the first baseline CQI comprising a first mapping of cement qualities to normalized carbon-oxygen ratios;

obtain a second PNL for the well, the second PNL obtained via a second PN logging of the well conducted after casing the well, after the first PN logging of the well, and at a time when the mud effects for the well are not be present;

determine a second baseline CQI for the well based on the CBL and the second PNL, the second baseline CQI comprising a second mapping of cement qualities to normalized carbon-oxygen ratios;

determine a tuned CQI for the well based on the first baseline CQI and the second baseline CQI, the tuned CQI comprising a third mapping of cement qualities to normalized carbon-oxygen ratios;

obtain a follow-up PNL for the well, the follow-up PNL obtained via a follow-up PN logging of the well conducted after the second PN logging of the well, the follow-up PNL indicating carbon-oxygen ratios for the well at the time of the follow-up PN logging of the well; and determine an updated cement quality log (CQL) for the well based on the tuned CQI and the follow-up PNL for the well, the updated CQL comprising a mapping of cement quality values versus depth in the wellbore.

21. The system of claim 20, further comprising:
one or more multi-detector (MD) pulsed neutron (PN) logging tools configured to be run in a wellbore of a well to acquire log data for use in generating one or more PN logs (PNLs),
the first PN logging of the well being conducted using at least one of the one or more MD PN logging tools,
the second PN logging of the well being conducted using at least one of the one or more MD PN logging tools, and
the follow-up PN logging of the well being conducted using at least one of the one or more MD PN logging tools.

* * * * *